(12) United States Patent
Ritchart et al.

(10) Patent No.: US 6,280,398 B1
(45) Date of Patent: Aug. 28, 2001

(54) METHODS AND DEVICES FOR COLLECTION OF SOFT TISSUE

(75) Inventors: Mark A. Ritchart, Murrieta; George White, Diamond Bar, both of CA (US)

(73) Assignee: Ethicon Endo-Surgery, Cincinnati, OH (US)

( * ) Notice: Subject to any disclaimer, the term of this patent is extended or adjusted under 35 U.S.C. 154(b) by 0 days.

(21) Appl. No.: 09/420,339

(22) Filed: Oct. 18, 1999

(51) Int. Cl.$^7$ ..................................................... A61B 10/00
(52) U.S. Cl. ............................................................. 600/564
(58) Field of Search ................... 600/564, 562, 600/565, 566, 567, 568, 571

(56) References Cited

U.S. PATENT DOCUMENTS

| | | |
|---|---|---|
| 2,113,246 | 4/1938 | Wappler . |
| 3,850,162 | 11/1974 | Iglesias . |
| 4,325,374 | 4/1982 | Komiya . |
| 4,362,160 | 12/1982 | Hiltebrandt . |
| 4,782,840 | 11/1988 | Martin, Jr. et al. . |
| 4,801,803 | 1/1989 | Denen et al. . |
| 4,889,991 | 12/1989 | Ramsey et al. . |
| 4,893,013 | 1/1990 | Denen et al. . |
| 4,959,547 | 9/1990 | Carroll et al. . |
| 5,014,708 | 5/1991 | Hayashi et al. . |
| 5,036,201 | 7/1991 | Carroll et al. . |
| 5,047,027 | 9/1991 | Rydell . |
| 5,064,424 | 11/1991 | Bitrolf . |
| 5,070,878 | 12/1991 | Denen . |
| 5,111,828 | 5/1992 | Kornberg et al. . |
| 5,119,818 | 6/1992 | Carroll et al. . |
| 5,133,360 | 7/1992 | Spears . |
| 5,133,713 | 7/1992 | Huang et al. . |
| 5,148,040 | 9/1992 | Wise, Jr. et al. . |
| 5,151,598 | 9/1992 | Denen . |
| 5,159,925 | 11/1992 | Neuwirth et al. . |
| 5,170,055 | 12/1992 | Carroll et al. . |
| 5,186,714 | 2/1993 | Boudreault et al. . |
| 5,201,731 | 4/1993 | Hakky . |
| 5,221,281 | 6/1993 | Klicek . |
| 5,246,005 | 9/1993 | Carroll et al. . |
| 5,282,800 | 2/1994 | Foshee et al. . |
| 5,304,176 | 4/1994 | Phillips . |
| 5,312,327 | 5/1994 | Bales et al. . |
| 5,334,183 | 8/1994 | Wuchinich . |
| 5,348,555 | 9/1994 | Zinnanti . |

(List continued on next page.)

FOREIGN PATENT DOCUMENTS

| | | |
|---|---|---|
| 31 48 306 A1 | 6/1983 | (DE) . |
| 0 593 929 A1 | 4/1994 | (EP) . |
| WO 89/10092 | 11/1989 | (WO) . |
| WO 95/08291 | 3/1995 | (WO) . |

OTHER PUBLICATIONS

"Techniques of Laparoscopic Morcellation of the Spleen" M.J. Legrand et al.: Minimally Invasive Therapy & Applied Technology 1996: vol. 5: No. 2; pp. 143–146.

Surgical resection and radiolocalization of the sentinel lymph node in breast cancer using a gamma probe; Krag et al. —Surgical Oncology 1993; 2; 335–340.

*Primary Examiner*—Robert L. Nasser
*Assistant Examiner*—Brian Szmal
(74) *Attorney, Agent, or Firm*—Bernard Shay

(57) ABSTRACT

A tissue sampling apparatus comprises a tubular body having a primary lumen for receiving a tissue sample. The tubular body includes a distal end, a proximal end, and a longitudinal axis extending from the proximal end to the distal end. The tissue sampling apparatus further comprises a cutting cylinder having a distal cutting edge, which is movable both distally and proximally relative to the tubular body. A band having an eyelet disposed therein extends across a distal end of the tissue sampling apparatus, wherein the eyelet is advantageously movable relative to the distal cutting edge in order to sever a distal end of the tissue sample.

19 Claims, 13 Drawing Sheets

U.S. PATENT DOCUMENTS

| | | |
|---|---|---|
| 5,383,456 | 1/1995 | Arnold et al. . |
| 5,395,312 | 3/1995 | Desai . |
| 5,400,564 | 3/1995 | Humphries et al. . |
| 5,403,311 | 4/1995 | Abele et al. . |
| 5,429,133 | 7/1995 | Thurston et al. . |
| 5,441,050 | 8/1995 | Thurston et al. . |
| 5,441,503 | 8/1995 | Considine et al. . |
| 5,456,689 | 10/1995 | Kresch et al. . |
| 5,475,219 | 12/1995 | Olson . |
| 5,495,111 | 2/1996 | Thurston et al. . |
| 5,526,822 | 6/1996 | Burbank et al. . |
| 5,527,331 | 6/1996 | Kresch et al. . |
| 5,575,293 | 11/1996 | Miller et al. . |
| 5,649,547 | 7/1997 | Ritchart et al. . |
| 5,769,086 | 6/1998 | Ritchart et al. . |
| 5,775,333 | 7/1998 | Burbank et al. . |
| 5,810,806 | 9/1998 | Ritchart et al. . |
| 5,913,857 | 6/1999 | Ritchart et al. . |
| 5,928,164 | 7/1999 | Burbank et al. . |
| 5,980,469 | 11/1999 | Burbank et al. . |

METHODS AND DEVICES FOR COLLECTION OF SOFT TISSUE

FIELD OF THE INVENTION

The present invention relates to methods and devices for tissue sampling, and more specifically to improved instruments and methods for acquiring soft body tissue.

BACKGROUND OF THE INVENTION

It is often desirable and frequently necessary to sample or test a portion of tissue from humans and other animals, particularly in the diagnosis and treatment of patients with cancerous tumors, pre-malignant conditions, and other diseases or disorders.

Typically, in the case of breast cancer, there is a great emphasis on early detection and diagnosis through the use of screening modalities, such as physical examination, and particularly mammography, which is capable of detecting very small abnormalities, often nonpalpable. When the physician establishes by means of a mammogram or other screening modality that suspicious circumstances exist, a biopsy must be performed to capture tissue for a definitive diagnosis as to whether the suspicious lesion is cancerous. Biopsy may be done by an open or percutaneous technique. Open biopsy, which is an invasive surgical procedure using a scalpel and involving direct vision of the target area, removes the entire mass (excisional biopsy) or a part of the mass (incisional biopsy). Percutaneous biopsy, on the other hand, is usually done with a needle-like instrument through a relatively small incision, blindly or with the aid of an artificial imaging device, and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment of tissue is obtained for histologic examination which may be done via a frozen section or paraffin section.

The type of biopsy utilized depends in large part on circumstances present with respect to the patient, including the location of the lesion(s) within the body, and no single procedure is ideal for all cases. However, core biopsy is extremely useful in a number of conditions and is being used more frequently by the medical profession.

A very successful type of image guided percutaneous core breast biopsy instrument currently available is a vacuum-assisted automatic core biopsy device. One such successful biopsy device is shown and disclosed in U.S. Pat. No. 5,526,822, U.S. Pat. No. 5,649,547, and U.S. Pat. No. 5,769,086, all of which are commonly owned by the assignee of the present application and are herein expressly incorporated by reference. This device, known commercially as the MAMMOTOME® Biopsy System, has the capability to active capture tissue prior to cutting the tissue. Active capture allows for sampling through non-homogeneous tissues, meaning that the device is equally capable of cutting through hard and soft tissue. The device is comprised of a disposable probe, a motorized drive unit, and an integrated vacuum source. The probe is made of stainless steel and molded plastic and is designed for collection of multiple tissue samples with a single insertion of the probe into the breast. The tip of the probe is configured with a laterally disposed sampling notch for capturing tissue samples. Orientation of the sample notch is directed by the physician, who uses a thumbwheel to direct tissue sampling in any direction about the circumference of the probe. A hollow cylindrical cutter severs and transports tissue samples to a tissue collection chamber for later testing.

While the MAMMOTOME Biopsy System functions very well as a core biopsy device, there are occasions when, because of the size of a lesion, or its location, it may be advantageous to use a core biopsy device of a type disclosed in U.S. Pat. No. 5,111,828, to Kornberg et al., also expressly incorporated by reference herein, wherein the tissue receiving port is disposed at the distal end of the device and is oriented axially rather than laterally. A disadvantage of this type of device, however, is the lack of ability to effectively and efficiently draw tissue into the receiving chamber prior to and during the tissue cutting process. A second disadvantage is the requirement to withdraw the device from parent tissue and remove the first specimen, reassemble the device, then reintroduce the device for each desired specimen. A third disadvantage is the necessity of manually handling each specimen obtained.

On other occasions, the ability to sample any selected area of a cavity wall from within the cavity may be important, which ability requires the use of a flexible probe.

Furthermore, it is desirable during the biopsy process to "stage" the spread of a cancer. For example, breast cancer starts in the milk ducts, the mammary glands. The initial change towards breast cancer is now thought to be the development of atypical ductile hyperplasia. The next step is thought to be represented by ductile carcinoma in situ. Finally, the last step in the development of breast cancer is infiltrating ductile carcinoma. By the time the breast cancer has reached the stage of infiltrative ductile carcinoma, breast cancer cells have developed the ability to migrate from the duct of origin, disassociate themselves from one another, and enter vascular structures, such as the lymphatic channels. When these malignant infiltrative ductile carcinoma cells enter the vascular system, they can spread or metastasize to other parts of the body. It is this metastatic process that ultimately leads to death from breast cancer.

When breast cancer cells enter the lymphatic system, they metastasize in an orderly fashion to regional lymph nodes. Drainage can occur to the axillary lymph nodes, the supraclavicular lymph nodes, the lateral thoracic lymph nodes, and to the internal mammary lymph nodes.

It is the current standard of practice to determine if breast cancer cells have extended to regional lymph nodes by surgically performing an axillary lymph node dissection known as lymphadenectomy. In this open surgical procedure, a relatively large incision (5–10 cm), is made at the axilla (the armpit). Through this incision, a relatively large volume (15 to 30 grams) of fatty tissue and lymph node tissue are removed.

During this process, anywhere from 10 to 30 lymph nodes can be recovered and submitted to pathology, where each of these lymph nodes is examined for the presence or absence of metastatic breast cancer. Based on positive lymph node findings, systemic therapy will be given to the patient with breast cancer, including chemotherapy. If, on the other hand, the lymph nodes of the axilla are free of metastatic disease, then the use of systemic therapies is limited.

Surgical lymphadenectomy carries a low mortality, but high morbidity. The most common morbidity is the development of lymph edema in the arm, which is ipsilateral to the axilla dissected. The development of lymph edema in the ipsilateral arm is, at times, a debilitating complication.

It has been shown in the examination of lymphatic drainage of melanoma, and now shown in the lymphatic drainage of breast cancers, that lymphatic drainage patterns can be defined by the injection of a radioisotope (or other traceable marker such as blue dye) into the bed of the tumor.

The isotope (or dye) is then followed, either visually, with a gamma camera imaging system, or with a Geiger counter-type of counting system.

The spread of cancer cells is orderly, the first lymph node reached by the drainage channels from the infected breast containing the most cancer cells. Consequently, the first lymph node in the draining system is referred to as the "sentinel" lymph node.

It has been further shown, if one simply removes the sentinel lymph node, the determination of whether or not breast cancer has metastasized to the regional lymph nodes of the axilla can be established without excision of the remaining lymph nodes in the axilla. The surgical removal of only one lymph node greatly reduces the complications of lymph node surgery including the morbidity of lymph edema.

It would be desirable to further reduce the morbidity of the axillary sentinel lymph node biopsy if instrumentation were available to allow the sentinel lymph node to be identified and removed percutaneously with as little effect as possible to the surrounding tissue structure. The apparatus described in this patent can be introduced percutaneously through a small skin opening and directed to the sentinel lymph node thus eliminating open surgical exploration. Consequently, sentinel lymph node biopsy could be accomplished as an office procedure, eliminating hospitalization and minimizing the recovery period.

The elements of a percutaneous sentinel lymph node biopsy are as follows: The tumor site in the breast is injected with a radioisotope (such as technicium 99 m labeled sulfur colloid) which travels via the lymphatic channels to the sentinel lymph node. The sentinel lymph node then becomes radioactively visible, or "hot." The apparatus hereafter described is able to identify or locate the radioactive lymph node through auditory and other signals, indicating when the apparatus is adjacent to the sentinel lymph node. The apparatus is further able to then characterize or "visualize" the surrounding tissue with the associated ultrasound portion of the apparatus. It is important to identify the associated structures adjacent to the lymph node, because relatively large blood vessels (arteries, veins,) and nerves traverse the axilla. With the combination of percutaneous Geiger counter identification and percutaneous ultrasound identification, the sentinel lymph node can be identified and biopsied without entering a major blood vessel or severing a major nerve.

With a small entry site, no suturing would be required (the procedure would be percutaneous), and the patient could be sent home with a simple band-aid over the axillary entry site. The following day, the patient would receive the results of the percutaneous sentinel lymph node biopsy determining whether or not metastatic disease is present or absent in the sentinel lymph node draining the affected breast.

Instruments are known in the prior art which could be adapted to perform some of the procedures outlined above. For example, U.S. Pat. No. 5,111,828 to Komberg et al. discloses a percutaneous excisional breast biopsy device having a cannula, open distal and proximal ends, and a sharp cutting surface on the distal end. A stylet extends through the cannula and includes a distal puncturing end. A localization guide wire is used to direct the instrument to a biopsy site. The cannula is moved distally to cut a desired tissue specimen, after which a descending element is pushed to the distal end of the tissue specimen, then pulled proximally to sever the specimen completely from surrounding tissue.

A significant disadvantage of the Kornberg approach is that only one tissue sample may be obtained for each insertion of the instrument into the patient's body to the biopsy site. Once the descending element has been pulled to sever the tissue sample, there is no opportunity to repeat the procedure while the instrument remains in place. Also, no means is provided to ensure that tissue to be sampled is drawn toward the distal end of the cannula 2 (or "actively captured"), thereby reducing tissue sampling efficiency.

SUMMARY OF THE INVENTION

The present invention lacks the disadvantages and shortcomings of the prior art and provides an improved method and device for percutaneous excisional tissue biopsy. The present invention may be used for purposes others than percutaneous biopsy. For example, the device may be used for general organ and tissue removal through a trocar to perform various laparoscopic procedures including splenectomy, nephrectomy, appendectomy and liver removal. The device may also be used laparascopically through a trocar to remove abnormal growths such as polyps.

More particularly, the invention provides an inventive tissue sampling probe which offers many advantages over probes available in the prior art. Unexpectedly superior results are obtained in connection with the retrieval of intact tissue specimens, because of a unique combination of cutting features. A particularly important feature of the invention is the ability to manipulate the cutting element to cleanly sever the distal end of the tissue specimen. In the preferred embodiments, this is accomplished without any cutting impact on surrounding tissue. The versatility of the invention permits its use in many applications, including, for example, breast biopsies, intraoperative staging, laparascopic surgery, and lymphadenectomy procedures.

More particularly, in one aspect of the invention, there is provided a tissue sampling apparatus which comprises a tubular body having a primary lumen for receiving a tissue sample. The tubular body includes a distal end, a proximal end, and a longitudinal axis extending from the proximal end to the distal end. The tissue sampling apparatus further comprises a cutting cylinder having a distal cutting edge, which is movable both distally and proximally relative to the tubular body. A band having an eyelet disposed therein extends across a distal end of the tissue sampling apparatus, the eyelet being advantageously movable relative to the distal cutting edge in order to sever a distal end of the tissue sample.

In another aspect of the invention, there is provided a tissue sampling apparatus which comprises a tubular body having a primary lumen for receiving a tissue sample which has a distal end, a proximal end, and a longitudinal axis extending from the proximal end to the distal end. A severing element is advantageously provided which has an eyelet disposed therein and extending across a distal end of the tissue sampling apparatus, wherein the eyelet is movable relative to the tubular body in order to sever a distal end of the tissue sample.

In yet another aspect of the invention, there is disclosed a method of capturing a body tissue sample using a tissue sampling apparatus comprising a tubular body having a lumen extending therethrough and a distal end, a cutting element disposed at the distal end of the tubular body, an eyelet disposed at the distal end of the tubular body as well, for transverse movement across the distal end, and an actuator for moving the eyelet. The method comprises the steps of advancing the tubular body through a tissue portion a desired distance so that the cutting element cuts a tissue sample core as the tissue sample enters the lumen, and actuating the eyelet to move across the distal end of the tubular body to sever a distal end of the tissue sample core.

The invention, together with additional features and advantages thereof, may best be understood by reference to the following description taken in conjunction with the accompanying illustrative drawing.

DESCRIPTION OF THE INVENTION

Figure 1:
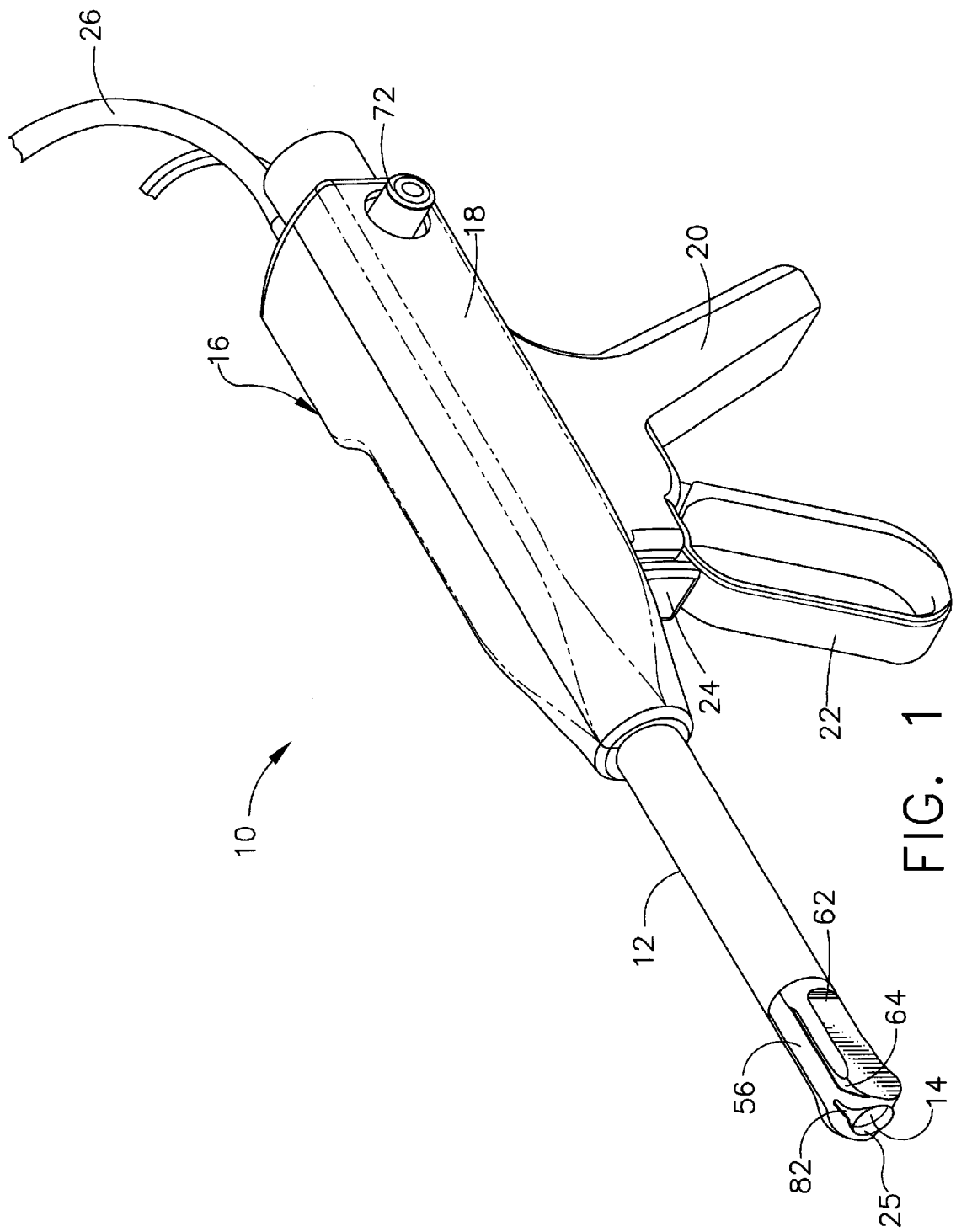
FIG. 1 is a perspective view of a first preferred embodiment of the inventive tissue sampling instrument.
Figure 2:
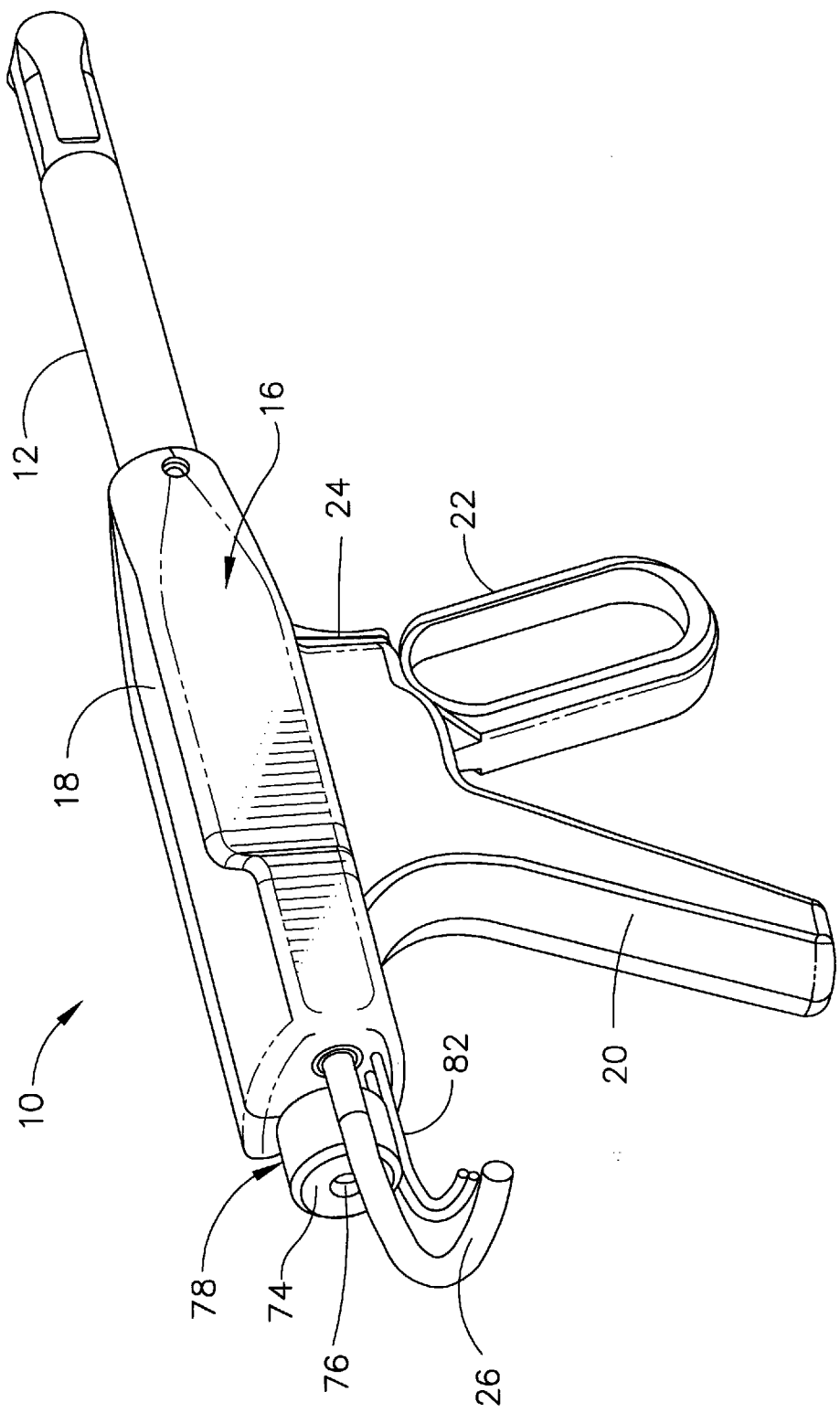
FIG. 2 is a perspective view, from an opposing side, of the inventive instrument shown in FIG. 1.
Figure 3:
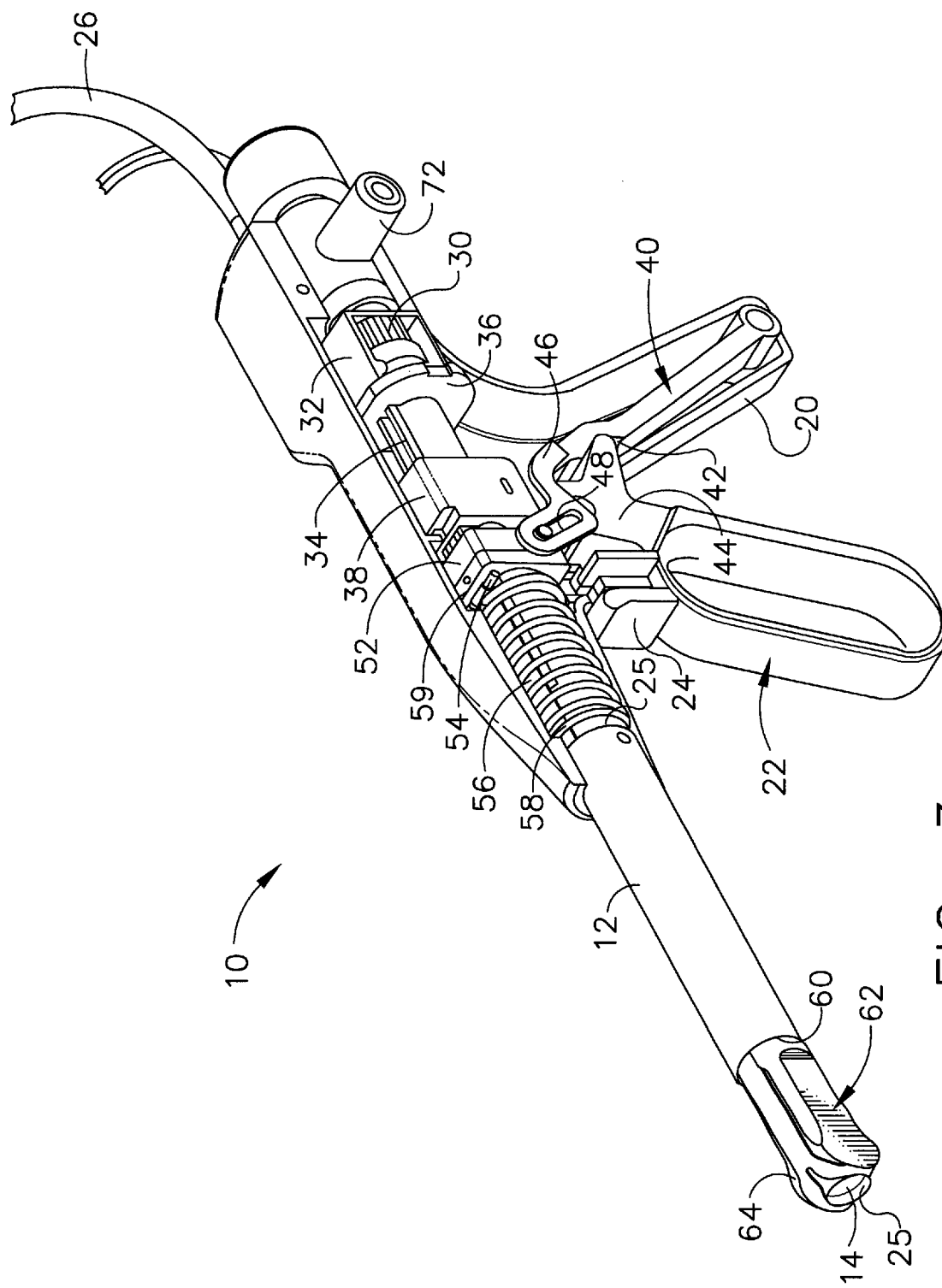
FIG. 3 is a perspective view similar to FIG. 1, with portions of the instrument housing removed to illustrate the internal construction of the inventive instrument.

Referring now more particularly to FIGS. 1–3, a first preferred embodiment of the invention is shown. The inventive tissue sampling probe 10 comprises a cylindrical outer sheath 12, and a lumen 14, which extends through the entire length of the probe 10.

The outer sheath 12 preferably comprises a biocompatible composite material such as a glass filament wound, epoxy-impregnated matrix material, for example, and preferably has a round cross-section, though other shapes may be used as well. Advantageous characteristics of the preferred composite material include light weight, durability, and ductility.

Figure 15:
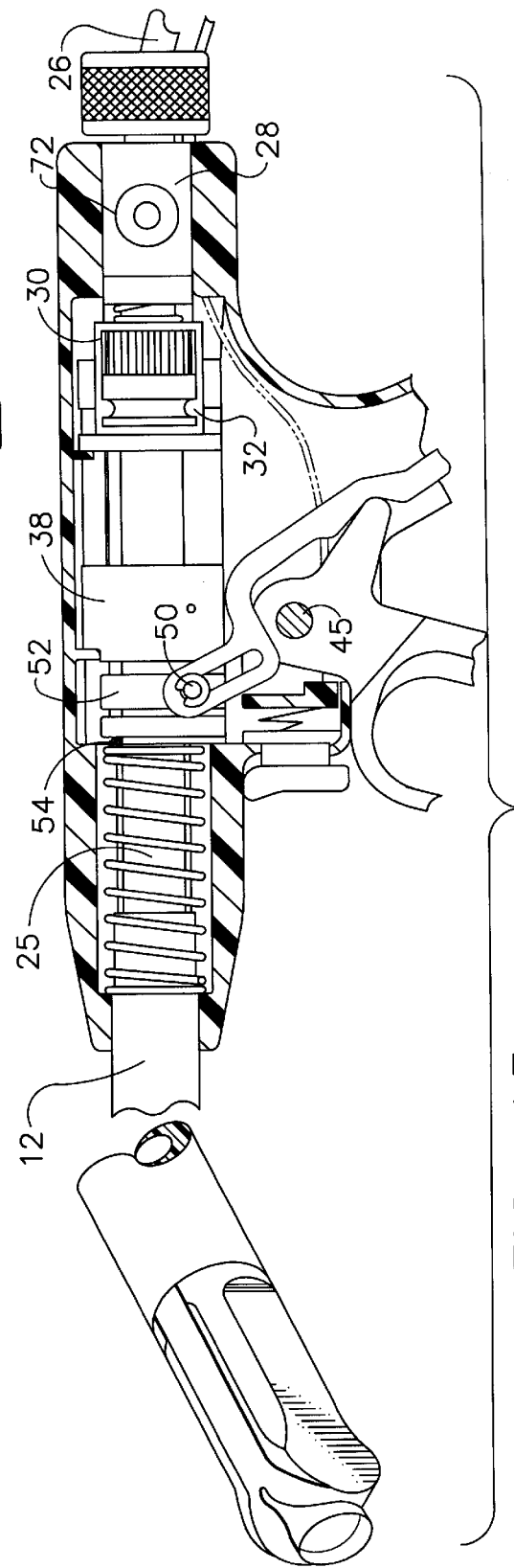
FIG. 15 is a cross-sectional view illustrating the internal working mechanism of the inventive instrument when the distal business end of the cutting instrument is in its initial position as shown in FIG. 4.
Figure 17:
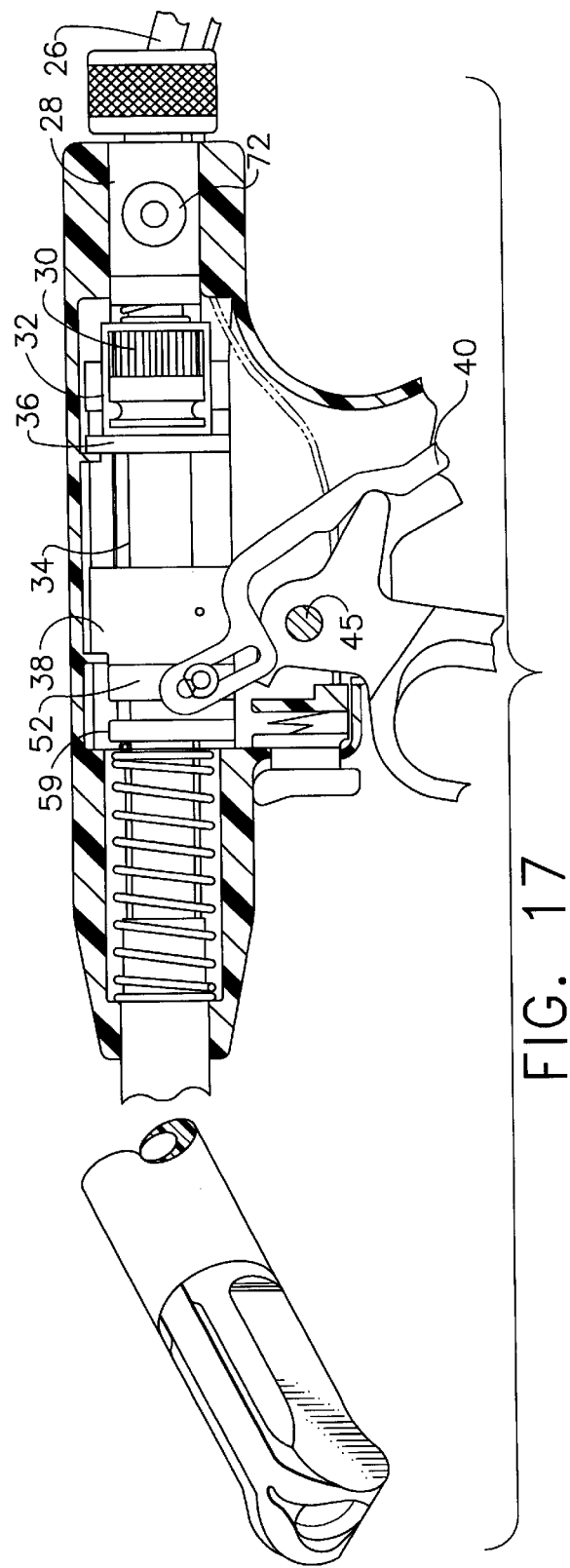
FIG. 17 is a cross-sectional view illustrating the internal working mechanism of the inventive instrument when the distal business end of the cutting instrument is in the configuration shown in FIG. 5.
Figure 19:
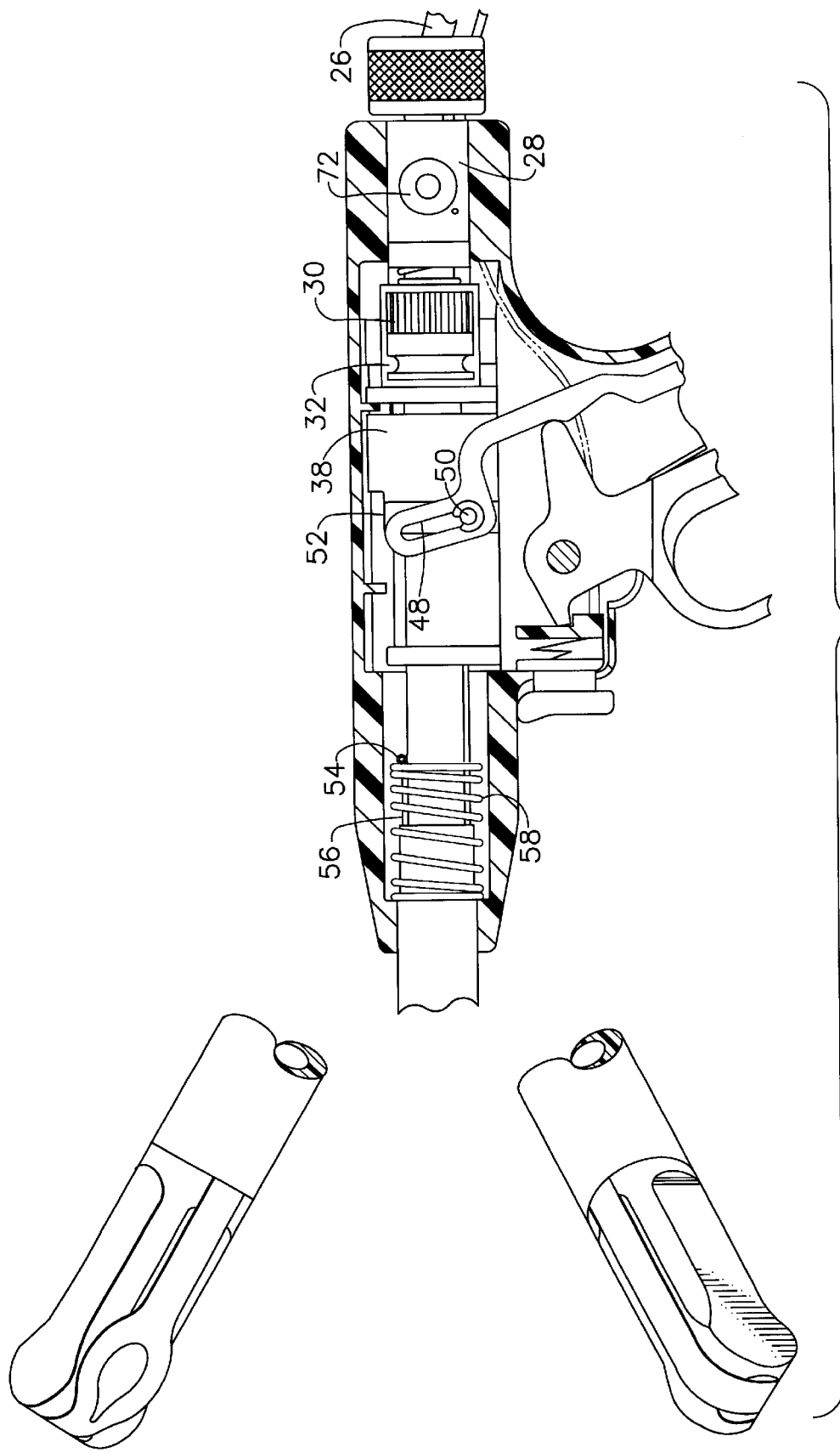
FIG. 19 is a cross-sectional view illustrating the internal working mechanism of the inventive instrument when the distal business end of the cutting instrument is in the configuration shown in FIGS. 7 and 8.
Figure 20:
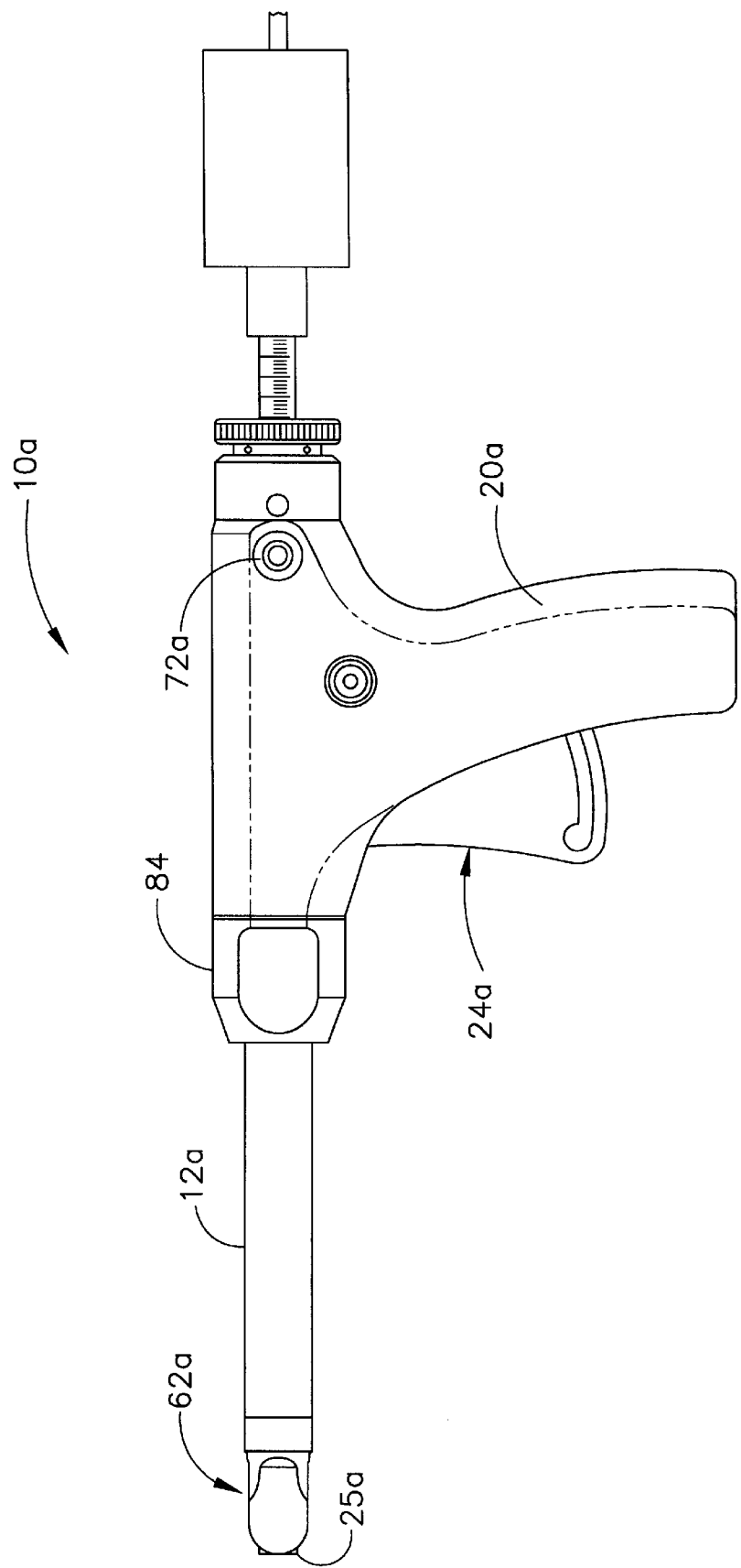
FIG. 20 is a schematic plan view from the side of a second modified embodiment of the inventive tissue sampling instrument.
Figure 21:
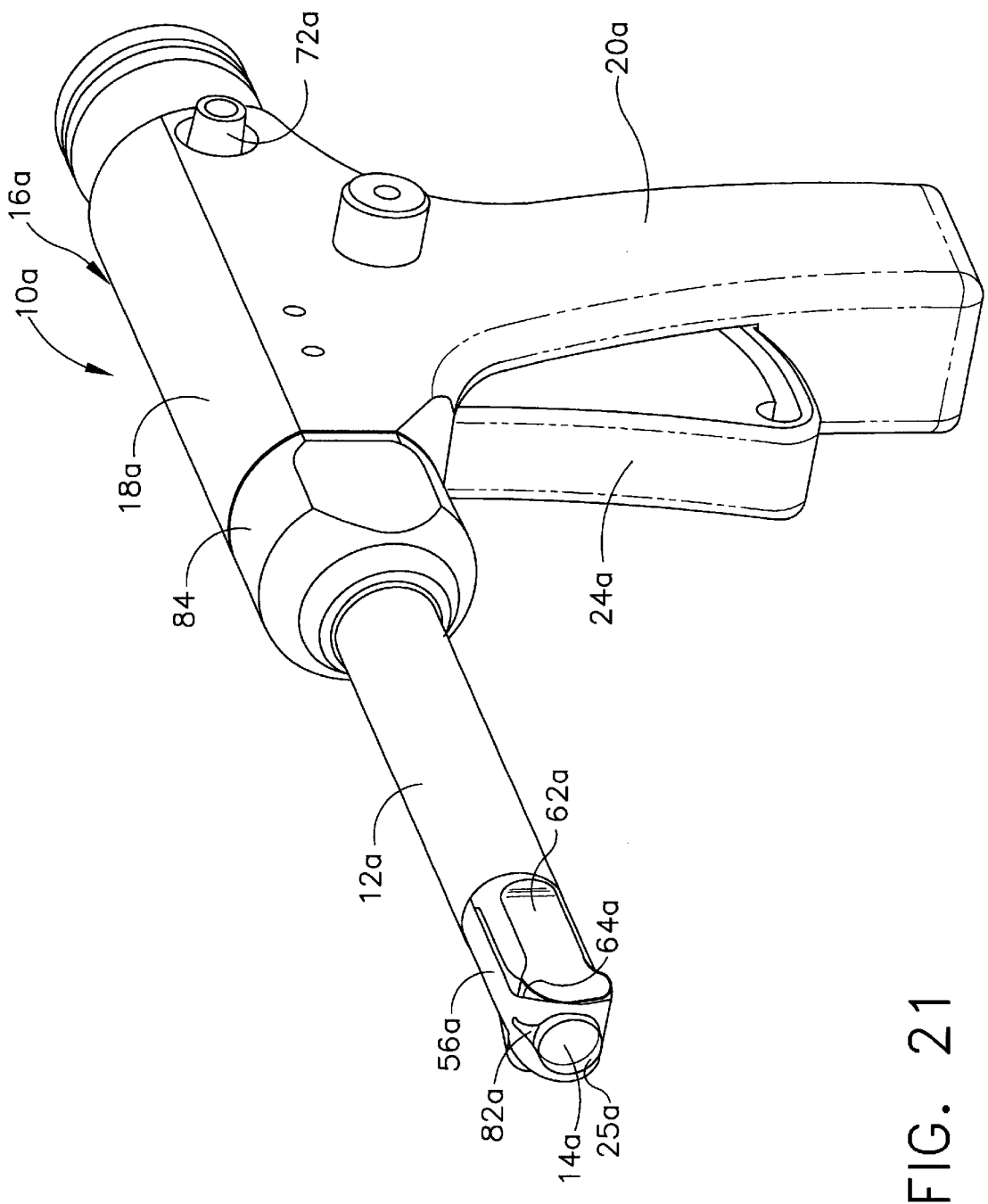
FIG. 21 is a perspective view of the inventive instrument illustrated in FIG. 20.
Figure 22:
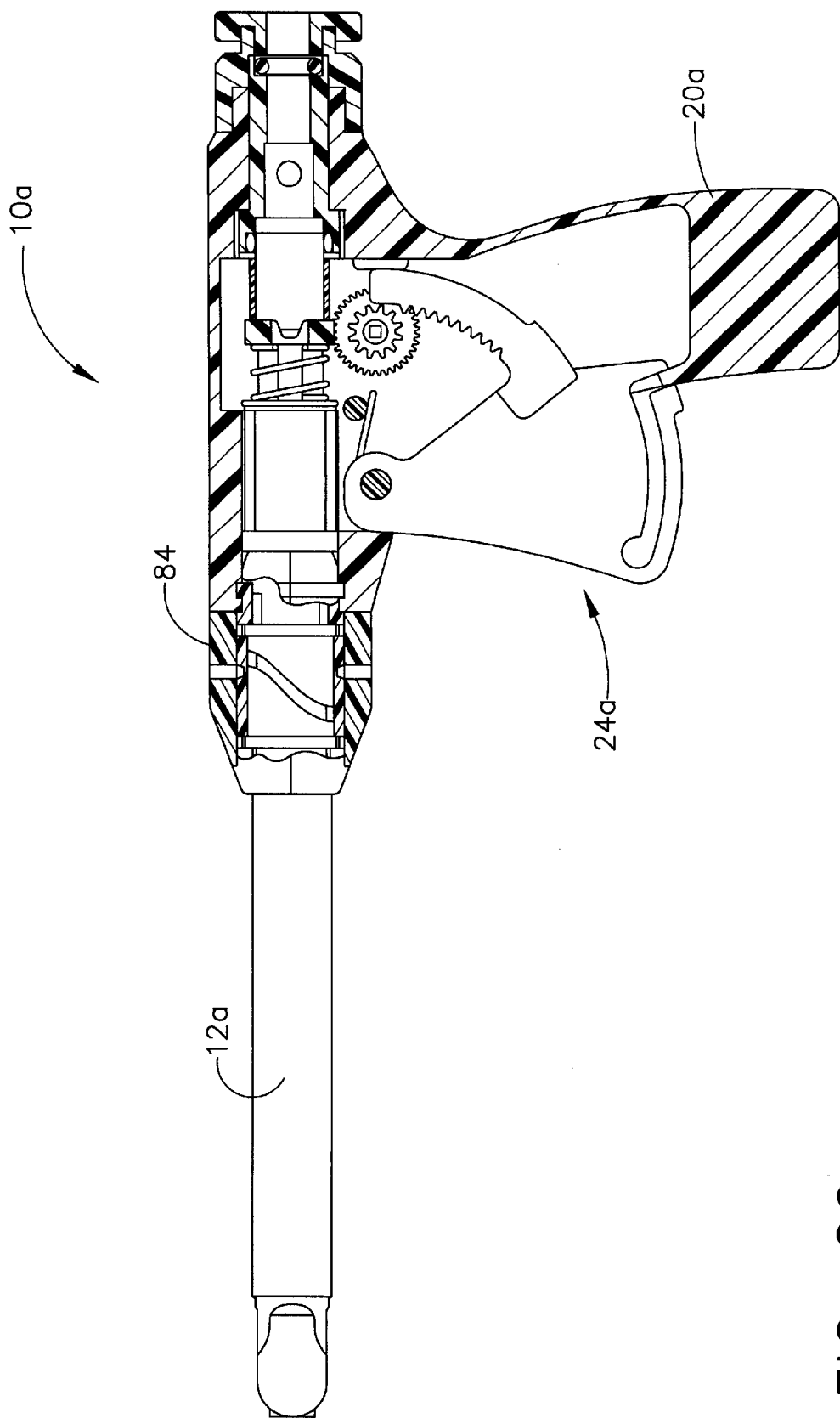
FIG. 22 is a cross-sectional side view illustrating the internal construction of the inventive instrument illustrated in FIGS. 20 and 21.
Figure 23:
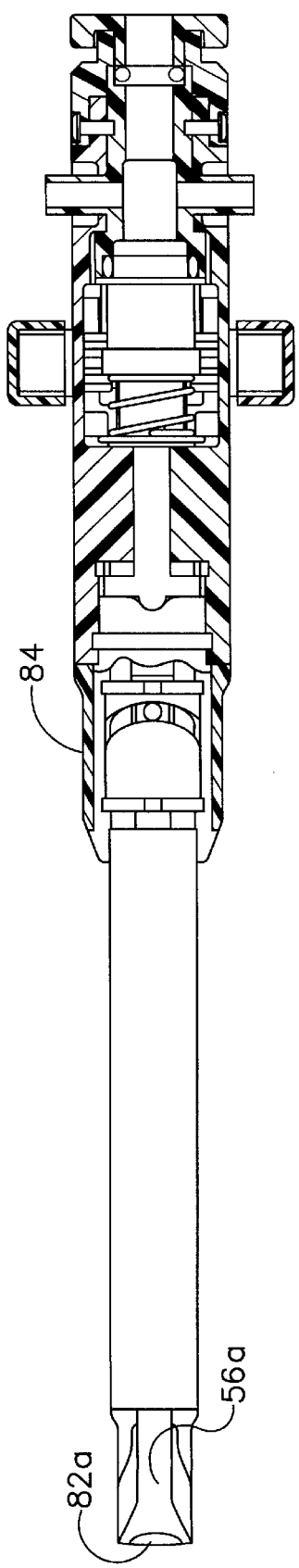
FIG. 23 is a cross-sectional top view of the inventive instrument illustrated in FIGS. 20–22.
Figure 24:
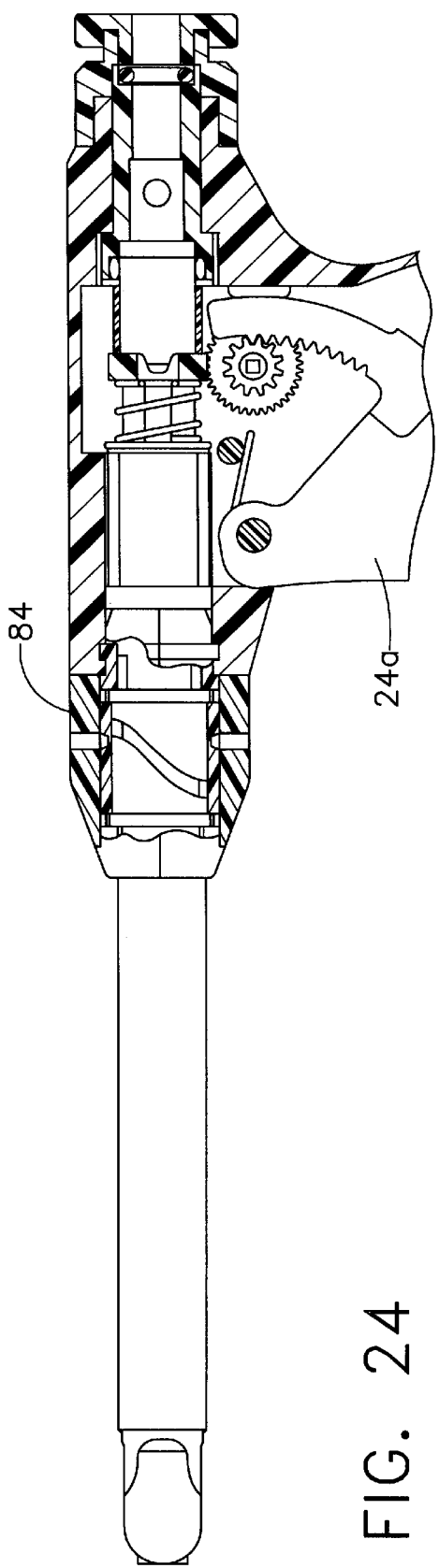
FIG. 24 is a cross-sectional fragmentary side view of the inventive instrument illustrated in FIGS. 20–23.

Disposed proximally of the outer sheath 12 is an actuator 16, which preferably comprises a housing 18, a fixed handle 20, a trigger 22, and a motor trigger 24. Disposed within the lumen 14, and extending along the length thereof, is an internal cylindrical cutter 25. In the illustrated preferred embodiment, the cutter 25 is selectively driven rotationally by means of a cable drive 26, which transfers rotational energy from an external motor or other power supply (not shown) through a drive gear 28 and a cutter gear 30 (FIGS. 15, 17, and 19). Alternatively, an internal motor disposed within the housing 18 could be provided. The motor trigger 24 actuates the cable drive to drive the gears 28 and 30, thereby selectively rotating the cutter 25, for a purpose to be described more fully hereinbelow.

Further with particular reference to FIGS. 3, 15, 17, and 19, which illustrate the internal construction of the inventive instrument 10, there is shown a cage 32 surrounding the cutter gear 30. Extending distally from the cage 32 is a rail 34, which is preferably constructed to be integral with the cage 32. The rail extends distally through a stop plate 36. A main carriage 38 is slidably disposed on the rail 34. A lever 40 is disposed in the fixed handle 20, the lever having a camming surface 42 which engages a camming portion 44 of the trigger 22. The camming portion 44 of the trigger is pivotably mounted on a pivot pin 45 (FIGS. 15, 17, 19). Integral with, or, alternatively, engageable with an inboard end of the lever 40 is an actuator portion 46 which includes a distal portion having a longitudinal slot 48. The slot 48 slidably engages a pin 50 which is disposed on a distal carriage 52. The distal carriage 52, like the main carriage 38, is slidable along the rail 34.

Figure 8:
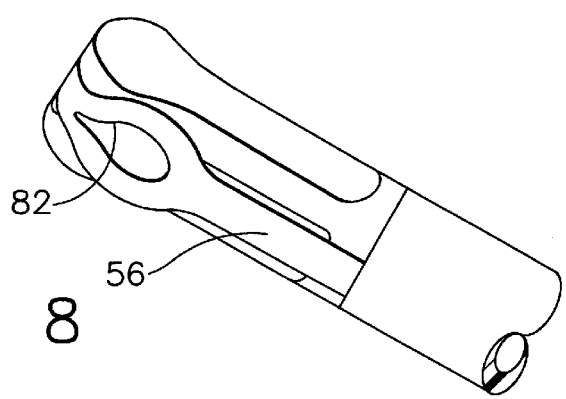

Distally of the distal carriage 52 is an eyelet pin 54, which is attached to one end of a flexible eyelet band 56. The flexible eyelet band 56 is preferably constructed of spring steel or other similar material. Disposed about the band 56 and internal cutter cylinder 25 is a compression spring 58, wherein the eyelet pin 54 is captured between the proximal end of the compression spring 58 and a fixed plate 59. The band 56 extends distally through the lumen 14 between the cutter cylinder 25 and the outer sheath 12. Distally of the distal edge 60 of the outer sheath 12, the probe 10 preferably comprises a shaped distal portion 62 having substantially flat surfaces 64 along which the eyelet band 56 may be disposed. The eyelet band 56 wraps about the distal end of the probe 10, as best seen in FIG. 8, and extends proximally again back along the distal portion 62 and then beneath the outer sheath 12. The band 56 is secured at its second end to the main carriage 38, using a pin attachment (not shown) similar to that obtained at its first end by means of pin 54, or other suitable fixed attachment means.

Figure 4:
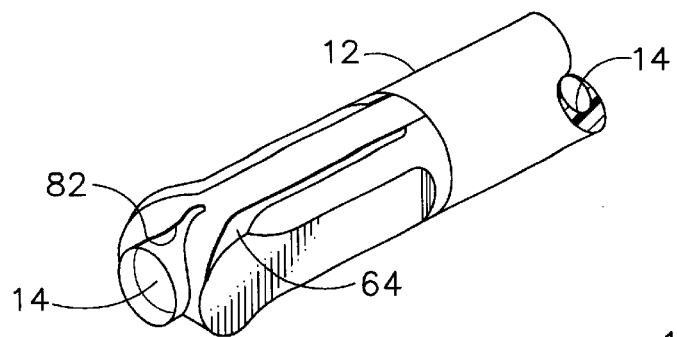
FIGS. 4–8 are perspective views of the distal end of the inventive instrument shown in FIG. 1, shown in isolation, illustrating sequentially the relative position of the eyelet cutter during a representative tissue specimen capturing procedure.
Figure 9:
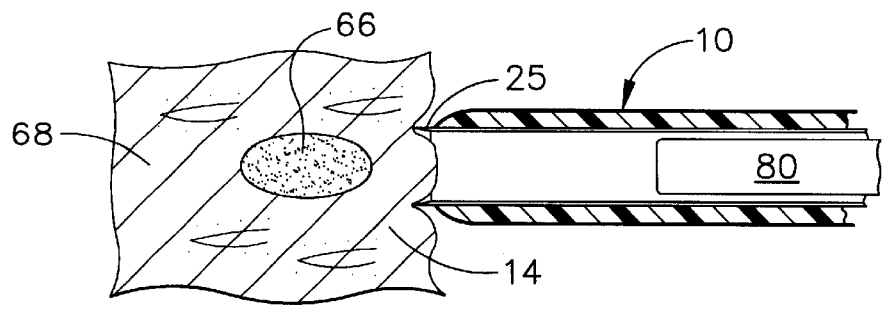
FIGS. 9–13 are schematic side views of the distal end of the inventive instrument shown in FIG. 1, illustrating sequentially the operation of the inventive eyelet cutter during a typical tissue capture procedure.
Figure 10:
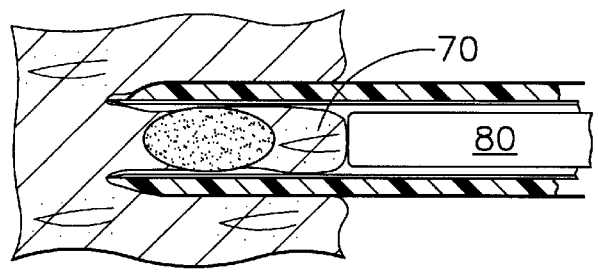
Figure 11:
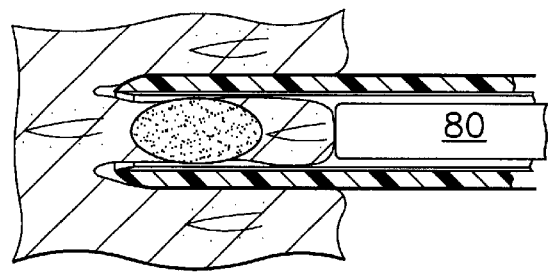
Figure 12:
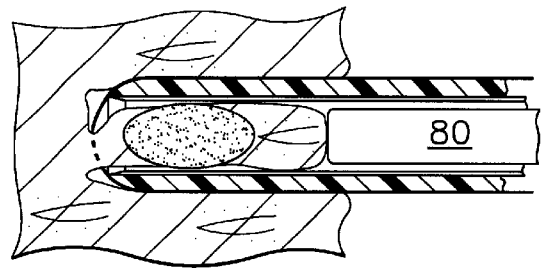
Figure 13:
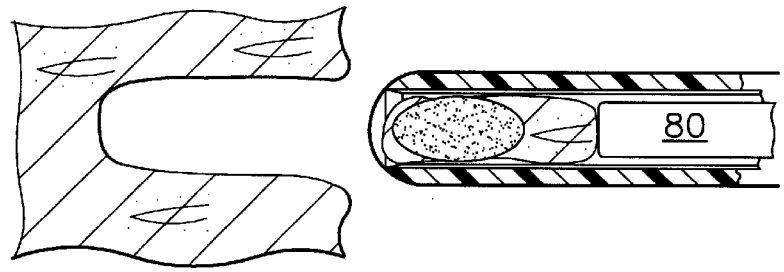
Figure 14:
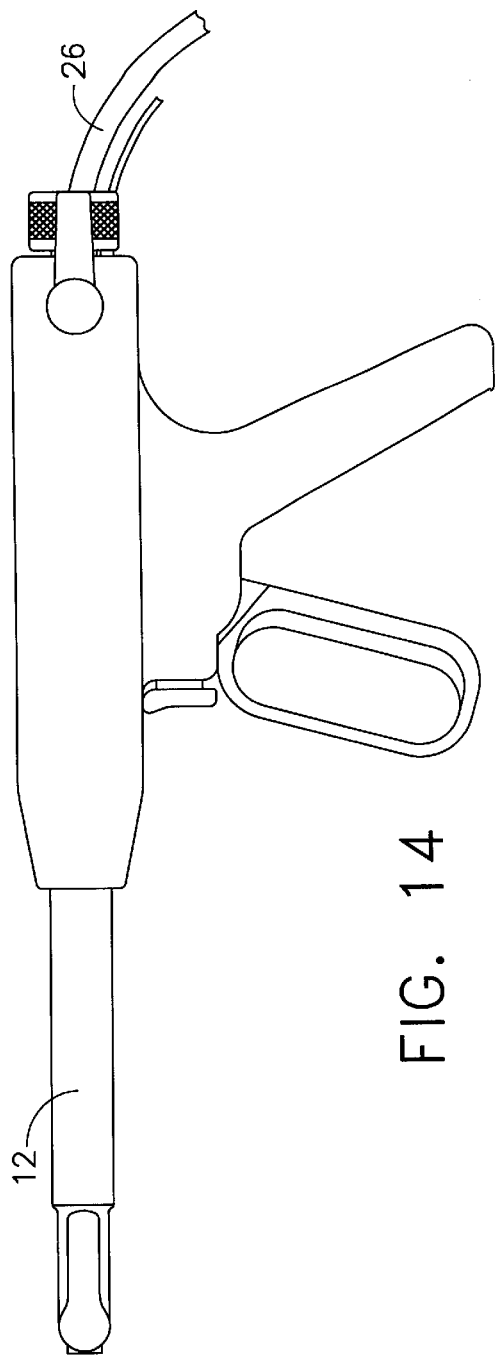
FIG. 14 is a schematic side view of the inventive instrument shown in FIG. 1, illustrating the instrument and the position of the trigger when the distal business end of the cutting instrument is in its initial position as shown in FIG. 4.

Now with particular reference to FIGS. 9–13, the operation of the inventive probe 10 will be described. Initially, as shown in FIG. 9, a lesion 66 within the tissue 68 of a patient is identified for removal by a physician. Accordingly, again as shown in FIG. 9, using known image guidance techniques, the instrument 10 is positioned outside of the patient's body at a point proximal to the target lesion 66. Then, with the cutter 25 extended, the probe 10 is advanced distally into the tissue 68, as illustrated in FIG. 10. The distal business end of the instrument 10 at this point in time, with the cutter 25 in an extended position, is illustrated in FIG. 4, while the configuration of the trigger and internal trigger mechanism during the acquisition step of FIGS. 10 and 4 is shown in FIGS. 14 and 15.

Simultaneously with advancement of the instrument 10, the motor trigger 24 is depressed by the practitioner, to thereby actuate the motor and cause rotation of the cutter 25 by means of drive gear 28 and cutter gear 30. With the cutter rotating, the advancement of the probe 10 easily slices through the tissue to create a tissue specimen 70 (FIG. 10) for capture within the lumen 14. In the preferred embodiment, depth marks (not shown) may be disposed axially along the exterior surface of the sheath 12 in order to assist the physician in determining when the instrument 10 has been advanced to the desired position.

In its preferred operational mode, the probe 10 functions to define and cut a tissue sample 70 having approximately the same diameter or cross-sectional shape as that of the lumen 14. Once a sample of adequate length has been secured, and the target lesion is fully contained within the lumen 14, advancement of the probe 10 is halted. At this point, the motor trigger 24 may be released to de-activate the motor, and thereby stop rotation of the cutter 25. Alternatively, depending upon the nature of a particular procedure, the practitioner may selectively actuate and stop the operation of the motor, as desired, during the balance of the procedure.

If desired, as an alternative to physical advancement of the probe 10 into the patient's body, as above described, a skin incision may be made in the patient's tissue 68 to form a pocket into which the probe 10 may be inserted. Then, a vacuum source (not shown), attached to the lumen 14 through a vacuum fitting 72, may be activated to draw a vacuum through the lumen 14, thereby drawing the desired tissue sample, including the lesion 66, into the lumen 14.

As discussed supra, in the Background of the Invention portion of the specification, a particularly useful purpose for the invention is to identify and target sentinel nodes for biopsy. Accordingly, the inventive instrument advantageously is designed to be used in connection with sensing probes for identifying and locating desired tissue (i.e. sentinel nodes) to be sampled. For example, ultrasound probes or radiation detecting (Geiger) probes may be employed, such as those disclosed in U.S. Pat. Nos. 4,959,547, 5,036,201, 5,119,818, 5,148,040, 5,170,055, and 5,246,005, which are assigned to Care Wise Medical Products Corporation of Morgan Hill, Calif., and are herein expressly incorporated by reference. Referring particularly now to FIG. 2, a probe fitting 74 is employed, which has an aperture 76 therein for direct connection with the lumen 14, from the proximal end 78 to the distal end of the instrument 10. The probe fitting 74 is configured to receive a sensing probe 80 (FIGS. 913).

A stand alone sensing probe 80 for use with the inventive instrument may comprise either an ultrasonic probe or a Geiger probe, both of which are conventionally known in the medical diagnostic arts. The sensing probe 80 is specifically configured to be inserted through the aperture 76 of the soft tissue acquisition device 10. Electronic control lines (not shown) extend from the proximal end of the sensing probe 80 to appropriate control units, for receiving and processing information obtained by the probe.

Alternatively, a multi-vision probe may be utilized. This type of sensing probe is capable of functioning both as an ultrasonic probe and as a Geiger probe, and has two sets of control lines for communicating with ultrasonic and Geiger electronic control units, respectively.

In operation, if a sensing probe 80 is utilized, the lesion 66 is located using the sensing probe, rather than the aforementioned imaging guidance equipment. The Geiger portion of the probe provides an X-Y location on the surface of the tissue to be sampled, while the ultrasonic portion provides depth information as well as X-Y location information. The sensing probe 80 may be retained in the lumen 14 during the acquisition procedure, in which case it can function as a tissue stop for the tissue sample being captured in the lumen 14, as shown in FIGS. 10–13.

Figure 5:
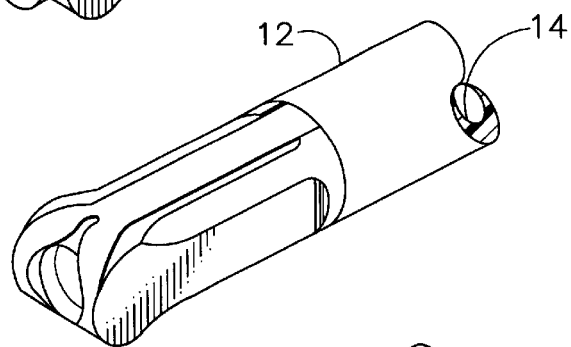
Figure 16:
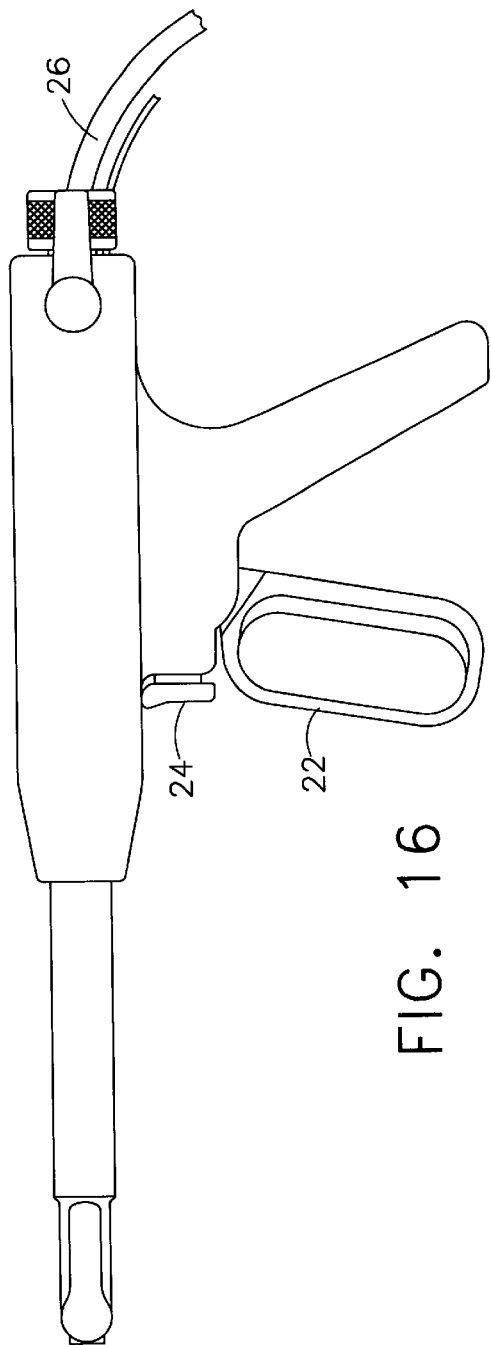
FIG. 16 is a schematic side view of the inventive instrument shown in FIG. 1, illustrating the instrument and the position of the trigger when the internal cylinder has been proximally retracted as shown in FIG. 5.

Once the tissue specimen has been captured within the lumen 14, the cutting cylinder 25 is retracted, as shown in FIGS. 11, 5, 16, and 17, by partially depressing the trigger 22 (FIGS. 16 and 17). This action causes the camming portion 44 of the trigger to pivot about the pivot pin 45 so that the camming surface of the lever 40 moves responsive to the pivoting of the camming portion 44 to exert a proximal pulling force on the pin 50 by its engagement with the longitudinal slot 48 on the actuator portion 46. Since the pin 50 extends from the distal carriage 52, the proximal movement of the pin 50 also causes the distal carriage 52 to be displaced proximally. This proximal displacement of the distal carriage 52 is illustrated in FIG. 17, relative to FIG. 15. As shown, in FIG. 17, the distal carriage has moved sufficiently proximally so that it is engaged with the main carriage 38, but not sufficiently to push the main carriage proximally. Because the cutter 25 is attached to the distal carriage 52, the proximal movement of the distal carriage 52 causes the cutter 25 to be retracted proximally, as shown in FIG. 5.

Figure 6:
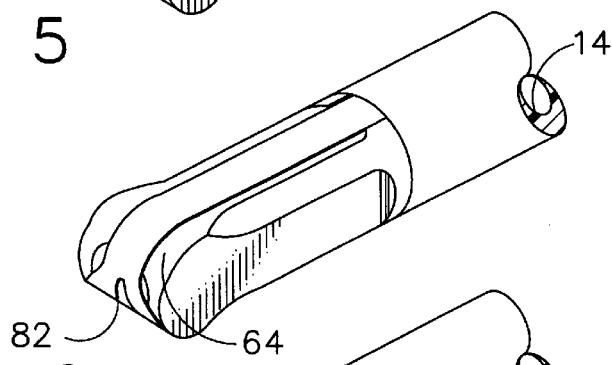
Figure 7:
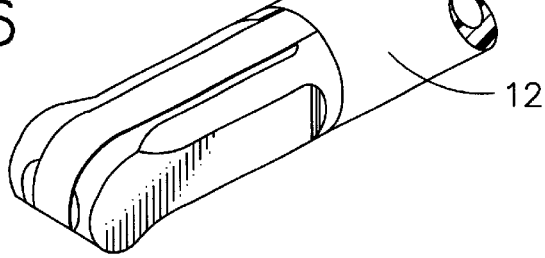
Figure 18:
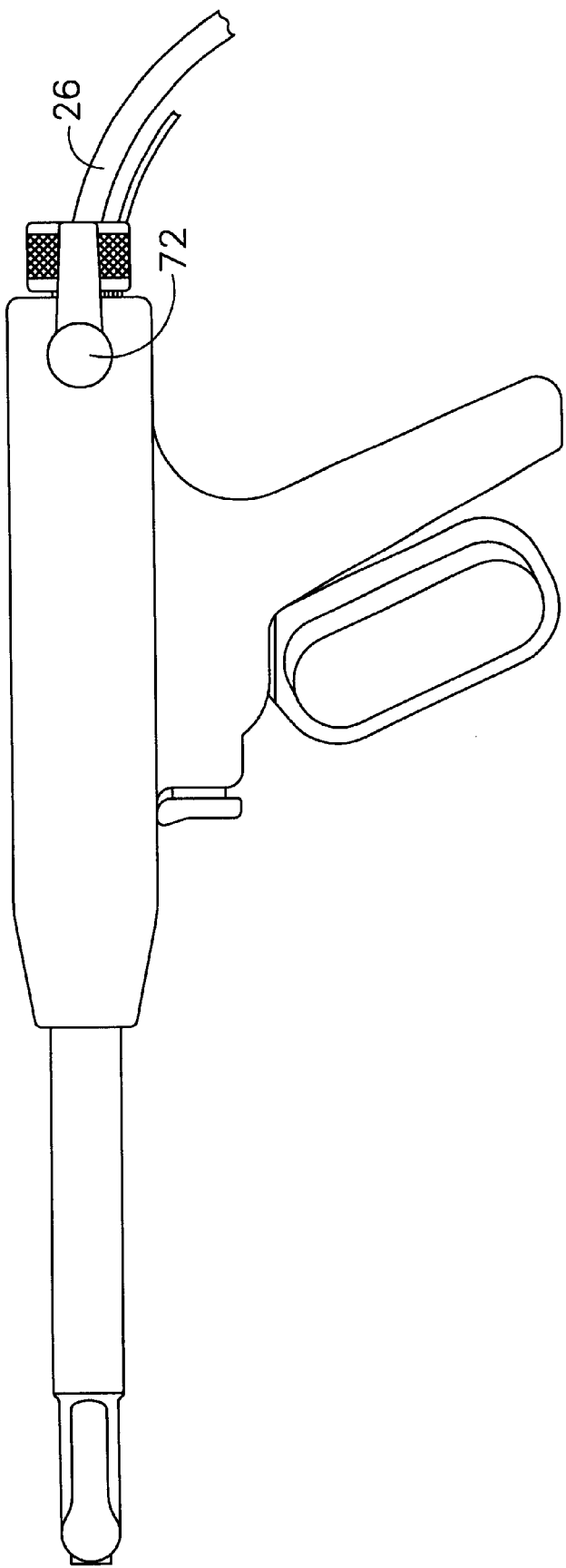
FIG. 18 is a schematic side view of the inventive instrument shown in FIG. 1, illustrating the instrument and the position of the trigger when the internal cylinder has been proximally retracted and the eyelet cutter has been actuated to rotate about the distal end of the instrument as shown in FIGS. 7 and 8.

The flexible eyelet band 56 includes an eyelet aperture 82 which ordinarily surrounds the extended cylindrical cutter 25 at the distal end of the instrument 10, as shown in FIG. 4. However, once the cutter has been retracted, as shown in FIG. 5, by the method above discussed, the band 56 is free to slide around the shaped distal portion 62 along the substantially flat surfaces 64, so that the eyelet bunches the distal end of the captured tissue specimen 70 and causes severance of the specimen distal end by the bunching action of the eyelet 82 of the tissue against the cutting surface of the cutter 25. The practitioner moves the eyelet band 56 as described, in order to sever the distal end of the tissue sample, by depressing the trigger fully, as shown in FIGS. 18 and 19. This action causes the distal carriage 52 to fully engage the main carriage 38 and to push it proximally, as shown in FIG. 19. As the main carriage moves proximally, the band 56 is pulled downwardly around the distal portion 62 of the instrument 10, as sequentially shown in FIGS. 6–8, so that the eyelet 82 moves downwardly around the edge and proximally for a predetermined distance along the lower surface of the shaped distal portion 62. By the time the eyelet 82 has fully moved past the lumen 14 and cutter 25, the distal end of the tissue specimen 70 will have been fully severed, so that the desired tissue specimen 70 including the target lesion 66 will have been fully captured within the lumen 14.

Once this procedure has been completed, one or more additional samples may be obtained and accommodated within the lumen if desired. To do so, the trigger is partially released so that the compression spring 58 will expand to bias the eyelet pin 54 proximally, thereby returning the flexible band 56 and eyelet 82 to their initial positions as shown in FIG. 5. Then, the trigger is released the remainder of the way to again extend the cutting cylinder 25 distally, as shown in FIG. 4. At this juncture the entire procedure may be repeated to obtain additional samples as desired, or until the lumen has reached its capacity. When the desired tissue samples have been obtained, the instrument may be removed from the patient's body so that the tissue sample(s) may be extracted and examined. In order to expedite tissue sample capture, the interior surface of the lumen 14 may be coated to reduce frictional contact between the lumen walls and the tissue sample as it travels therethrough.

Many other embodiments may be employed other than the embodiment illustrated in FIG. 1. For example, a modified embodiment is illustrated in FIGS. 20–24, wherein all elements corresponding to those of the embodiment of FIG. 1 are designated by like reference numerals, succeeded by the letter "a". In this embodiment, a cam nut 84 is provided on the actuator portion 16a, which is rotatable to a first position in order to initiate a camming action which retracts the cutting cylinder 25a, and to a second position in order to initiate a further camming action which moves the eyelet band 56a. In this embodiment, the trigger 24a operates the motor, but because of its construction, the practitioner has an ability to alternately squeeze and release the trigger 24a to create an oscillatory circular cutting action of the cylindrical cutter 25a. This oscillatory cutting action can be created by alternately activating and de-activating the motor, to cause the rotation of the cutter 25a to be alternately started and stopped, or the motor can be reversible, so that the alternate squeezing and releasing action of the practitioner actually causes the rotational direction of the cylinder to reverse.

While this invention has been described with respect to various specific examples and embodiments, it is to be understood that the invention is not limited thereto. For example, further embodiments could be developed which employed selected features of each of the embodiments disclosed herein. Additionally, in some circumstances, it may be desirable to construct the inventive device so that portions thereof which are exposed to a patient's blood and tissue during a procedure, such as the cutting cylinder and eyelet portions, and perhaps the entire tubular body, are disposable, and may be removable from the reusable actuator portion between procedures, for replacement with a new sterile cutting portion. Thus, it is clear that the disclosed invention can be variously practiced within the scope of the following claims.

What is claimed is:

1. A tissue sampling apparatus, comprising:
   a tubular body having a primary lumen for receiving a tissue sample, and having a distal end, a proximal end, and a longitudinal axis extending from said proximal end to said distal end;
   a cutting cylinder having a distal cutting edge and being movable both distally and proximally relative to said tubular body; and
   a band having an eyelet disposed therein and extending across a distal end of said tissue sampling apparatus, said eyelet being movable relative to said distal cutting edge in order to sever a distal end of said tissue sample.

2. The tissue sampling apparatus as recited in claim 1, wherein said tubular body comprises an outer sheath, and said cutting cylinder is disposed coaxially within said outer sheath.

3. The tissue sampling apparatus as recited in claim 2, wherein said cutting cylinder is selectively rotatable.

4. The tissue sampling apparatus as recited in claim 2, and further comprising an actuator disposed proximally of said tubular body.

5. The tissue sampling apparatus as recited in claim 4, wherein said actuator comprises a trigger for axially retracting and extending said cutting cylinder.

6. The tissue sampling apparatus as recited in claim 5, wherein said trigger also moves said band in order to move said eyelet relative to said distal cutting edge.

7. The tissue sampling apparatus as recited in claim 3, wherein said actuator comprises a trigger for selectively rotating said cutting cylinder.

8. The tissue sampling apparatus as recited in claim 4, wherein said actuator comprises a cam nut for axially retracting and extending said cutting cylinder.

9. The tissue sampling apparatus as recited in claim 8, wherein said cam nut also moves said band in order to move said eyelet relative to said distal cutting edge.

10. The tissue sampling apparatus as recited in claim 1, wherein said tubular body lumen is sized to accommodate a plurality of tissue samples.

11. A tissue sampling apparatus, comprising:
    a tubular body having a primary lumen for receiving a tissue sample, and having a distal end, a proximal end, and a longitudinal axis extending from said proximal end to said distal end; and
    a severing element having an eyelet disposed therein and extending across a distal end of said tissue sampling apparatus, said eyelet being movable relative to said tubular body in order to sever a distal end of said tissue sample.

12. The tissue sampling apparatus as recited in claim 11, and further comprising an actuator disposed proximally of said tubular body.

13. The tissue sampling apparatus as recited in claim 12, wherein said actuator is adapted to move said band in order to move said eyelet relative to said tubular body.

14. The tissue sampling apparatus as recited in claim 13, wherein said actuator comprises a trigger.

15. The tissue sampling apparatus as recited in claim 13, wherein said actuator comprises a cam nut.

16. The tissue sampling apparatus as recited in claim 11, and further comprising a cutting cylinder having a distal cutting edge and being movable both distally and proximally relative to said tubular body.

17. The tissue sampling apparatus as recited in claim 11, and further comprising a probe fitting having an aperture which communicates with said primary lumen, said probe fitting being configured to receive a sensing probe for locating a lesion in a patient's body.

18. A method of capturing a body tissue sample using a tissue sampling apparatus comprising a tubular body having a lumen extending therethrough and a distal end, a cutting element disposed at the distal end of the tubular body, an eyelet disposed at the distal end of the tubular body for transverse movement across said distal end, and an actuator for moving the eyelet, the method comprising:
    advancing the tubular body through a tissue portion a desired distance so that the cutting element cuts a tissue sample core as the tissue sample enters the lumen; and
    actuating the eyelet to move across the distal end of the tubular body to sever a distal end of the tissue sample core.

19. The method as recited in claim 18, wherein said tissue sampling apparatus includes a sensing probe disposed therein, the method further comprising a step of actuating said sensing probe to identify and locate a target lesion prior to advancing said tubular body.

* * * * *

UNITED STATES PATENT AND TRADEMARK OFFICE
CERTIFICATE OF CORRECTION

PATENT NO. : 6,280,398 B1
DATED : August 28, 2001
INVENTOR(S) : Mark A. Ritchart and George White It is certified that error appears in the above-identified patent and that said Letters Patent is hereby corrected as shown below:

<u>Column 3,</u>
Line 49, "band-aid" should read -- BAND-AID® Brand Adhesive Bandage --.

Signed and Sealed this

Eighteenth Day of June, 2002

Attest:

Attesting Officer

JAMES E. ROGAN
*Director of the United States Patent and Trademark Office*